(12) United States Patent
Whittle et al.

(10) Patent No.: US 6,350,478 B1
(45) Date of Patent: *Feb. 26, 2002

(54) ARTEMISIA JUDAICA FRACTIONATION METHOD

(75) Inventors: Brian Anthony Whittle, Hornsea; Paul Geoffrey Skett, Glasgow, both of (GB)

(73) Assignee: Phytotech Limited, Cambridgeshire (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/826,419

(22) Filed: Mar. 27, 1997

(30) Foreign Application Priority Data

Mar. 28, 1996 (GB) .............................................. 9606579

(51) Int. Cl.⁷ .............................................. A61K 35/78
(52) U.S. Cl. ...................................................... 424/740
(58) Field of Search .............................. 424/195.1, 740

(56) References Cited

U.S. PATENT DOCUMENTS 4,952,603 A * 8/1990 Elferaly et al. ............. 514/450

FOREIGN PATENT DOCUMENTS

| JP | 7-206839 | * | 8/1995 |
| WO | WO 94/00584 | * | 1/1994 |

OTHER PUBLICATIONS

"Hypoglycaemic effect of *Artemisia herba alba* II. Effect of a Valuable Extract on Some Blood Parameters in Diabetic Animals", Al–Shamaony et al, *Journal of Ethnopharmacology*, 43, No. 3, Jul. 22, 1994, pp. 167–171.

"Effects of *Artemisia pallens* Wall. on Blood Glucose Levels in Normal and Alloxan–Induced Diabetic Rats" Subramoniam et al, *Journal of Ethnopharmacology*, 50, No. 1, Jan. 1996, pp 13–17.

"Hypoglycaemic Effect of *Artemisia herba alba*. I. Effect of Different Parts and Influence of the Solvent on Hypoglycaemic Activity", Al–Khazraji et al, *Journal of Ethnopharmacology*, vol. 40, No. 3, Dec. 1993, pp. 163–166.

Peran et al., "Effect of a new hypoglycemic drug on the blood sugar in rats", Revista Iberica de Endocrinilogia, (Mar–Apr. 1976) 23 (134) pp. 171–178.*

Khafagy et al., "Glaucolide–like sesquiterpene lactones from *Artemisia judaica*" Phytochemistry, vol. 27, No. 4, pp. 1125–1128, (1988).*

Rodriguez de Vera et al., "Estudio preliminar de los effectos produdidos en la fraccion lipidica de diversos organos de rata tras la administracion de vulgarina", Bolletino Chimici Farmaceutico, 115(6), 1976, pp. 445–456.*

Saleh et al., "Flavonoids of *Artemisia judaica, A monosperma* and *A. herba–alba*", Phytochemistry, vol. 26, No. 11, pp. 3059–3064, 1987.*

* cited by examiner

Primary Examiner—Sandra E. Saucier
Assistant Examiner—Vera Afremova
(74) Attorney, Agent, or Firm—Larson & Taylor PLC

(57) ABSTRACT

Extracts of herbs of the Artemisia family, some of which have been known in traditional medicine to have antidiabetic effects, are fractionated chromatographically to remove unacceptable mutagenetic properties while retaining effectiveness against Diabetes mellitus. Certain fractions are found to be insulinomemetic while others have glucagon antagonistic properties. Mixtures of such fractions have optimum clinical effect.

9 Claims, 3 Drawing Sheets

*ARTEMISIA JUDAICA* FRACTIONATION METHOD

The present invention relates to compounds and compositions for use in the treatment of diabetes or other hyperglycaemic defects of carbohydrate metabolism, methods of making the compositions and methods of treating diabetes or other hyperglycaemic defects in carbohydrate metabolism by administration of said compounds or compositions.

Diabetes mellitus is a metabolic disorder in which the ability to oxidise carbohydrates is reduced or completely lost, resulting in hyperglycaemia (raised blood sugar), polyuria (increased output of urine) and glucosuria (appearance of sugars (e.g. dextrose) in the urine). Diabetes has been recognised as a major disease for centuries. In addition to defective carbohydrate metabolism, it can also lead to altered metabolism of lipids and proteins and patients are at risk of complications from vascular disease which are always serious and may be fatal.

Diabetes results from failure of the Islets of Langerhans ($\beta$) cells of the pancreas to produce sufficient insulin. It can also arise as a result of auto-immunity directed against Islet tissue and altered efficiency of insulin receptors. Temporary hyperglycaemia, which may not be sufficiently severe to be classified as diabetes, may occur due to hormonal imbalance during pregnancy.

Inositol (also known as meso-inositol, myo-inositol and cyclohexitol) is a growth factor and vitamin of the B complex which is widely distributed in plants and animals. Inositol appears to be involved physiologically in lipid metabolism and has been proposed as a second messenger for insulin.

The incidence of diabetes varies geographically and this is summarised in Table 1.

TABLE 1

Geographical Incidence of Diabetes

| Country | Incidence Per 100,000 | |
|---|---|---|
| | IDDM | NIDDM |
| UK | 17 | 200 |
| US | 18 | 440 (by 6th decade) |
| Northern Europe | 43 | 100–250 |
| Southern Europe | 8 | 800 |
| Japan | 1 | |

It is estimated that there is an equal number of undiagnosed cases. The morbidity and mortality associated with diabetes mellitus have prompted the search for effective treatments.

Current classification of diabetes mellitus (DM) distinguishes several types of disease and these have a bearing on treatment. Insulin-dependent diabetes mellitus (IDDM or Type I) is characterised by $\beta$-cell antibodies and zero endogenous insulin levels; these patients are dependent on exogenous insulin to prevent ketoacidosis and death, and respond only to insulin or insulinomimetics. Noninsulin-dependent diabetes mellitus (NIDDM or Type II) refers to a lack of $\beta$-cell antibodies, continued presence of endogenous insulin, and insulin resistance; these patients may or may not use insulin for symptom control but do not need it for survival. The symptoms of this type would be ameliorated by hypoglycaemics and by antagonists of glucagen. This group has been further sub-divided into obese and non-obese NIDDM. Other, hormonally induced forms of DM or DM due to pancreatic tissue damage are recognised. There is a spectrum of severity of diseases, for example "impaired glucose tolerance" is present when individuals have plasma glucose levels intermediate between normal and those considered to be diabetic.

The disease has been treated, across the spectrum of severity, with pharmaceutical preparations, although there are disadvantages attaching to each of the major types of therapeutic agent. This prompts the search for new drug treatments, particularly those that are active when taken orally.

The main types of drug treatment currently available are:

Insulin, obtained form animal pancreas or produced in genetically modified micro-organisms, is available in a variety of forms for parenteral use. Insulin is destroyed in the gastro-intestinal tract and is almost invariably given by injection.

The need for treatments which do not need to be given by injection has long-been recognised, and several types of anti-diabetic agents have been introduced. Medicines based on hypoglycaemic, anti-hyperglycaemic agents, $\alpha$-glucosidase inhibitors, and hydrocolloid substances are licensed by regulatory authorities for the treatment of diabetes mellitus. The main groups of antidiabetic agents include, but are not limited to, the following:

Sulphonylureas, for example gliclazide, are a group of agents which cause hypoglycaemia by stimulating insulin release from pancreatic $\beta$-cells.

Biguanides, exemplified by metformin, do not stimulate release of insulin but act by increasing the sensitivity of peripheral tissues to insulin.

$\alpha$-glucosidase inhibitors such as acarbose reduce intestinal absorption of carbohydrates and blunt the rise in plasma glucose which occurs after meals in both normal and diabetic subjects.

Several plant-based products, for example guar gum and ispaghula, contain colloidal substances which produce a bulky hydrated gel (soluble fibre) in the gastro-intestinal tract. The activity of this type of compound is essentially mechanical; when given with food the hydrated fibre entraps sugar and other carbohydrate molecules and slows down the absorption of carbohydrate from food. It thus blunts the postprandial rise in plasma glucose. Licensed products based on these actions are used as adjunctive therapy in the treatment of diabetes.

Each of the groups of orally active agents have limitations on efficacy and may also produce side effects. There is therefore a need for additional oral anti-diabetic agents which are effective and safe.

Some plant species have been claimed to contain antidiabetic constituents. A comprehensive review of plants which have been traditionally used for the treatment of diabetes has been published by Day (Phd thesis, Kings College School of Medicine and Dentistry, 1987) who also evaluated a number of these herbs including *Allium cepa, Momordica charantia,* and *Pterocarpus marsupium,*

*Artemisia judaica* is used in Libyan traditional medicine as an infusion for the treatment of "wasting disease", almost certain diabetes mellitus. Little scientific work has been done on this herb although various Artemisia species are known to have some pharmacological activity (see Table 2).

TABLE 2

Species of Artemisia used in Traditional Medicine

| Plant | Geographical Area | Traditional Use | Original or Review reference |
|---|---|---|---|
| Artemisia abysinica | Middle East | | Mossa 1985 |
| Artemisia absynthicum | Europe N Africa W Asia | Anthalmintic | Messague 1981 BHP 83 |
| Arcemisia afra | Africa | | Ajaonnther 1979 Watt & Breyer - Brandwijk 1962 |
| Artemisia cannariensis | | | Bever & Zahnd 1979 |
| Artemisia dracunculus | N America | | Farjou et al 1985 |
| Artemisia herba-alba | Middle East | Antidiabetic | Al-Waili 1986 Twaij & Al-Badr 1988 Farjou et al 1985 |
| Artemisia judaica | N Africa | Antidiabetic | Galal et al 1974 Abdalla & Zarga 1987 |
| Artemisia vulgaris | Europe | Appetite stimulant Anthelmintic Emmena- gogue | Farnsworth & Segelman 1971 Amor. Herbal Pharmacolog. Deleg 1975 BHP 1983 |

*Artemisia herba-alba*, a closely related herb from Iraq has been found have an anti-diabetic effect. (Al-Waili, 1986, 1988; Twaij and Al-Badr, 1988). Extracts of *Artemisia judaica* have been found to contain some active pharmacological agents (Gallal et al, 1974, Abdalla and Zarga, 1987). Subramoniam et al (J Ethno-pharmacology 50 (1996) 13–17) have investigated the effects of A Pallens on normal and alloxon-induced diabetic rats. They used aqueous methanol and acetone extracts of the plant.

The use of all the above plants is limited by their toxicity, especially their mutagenicity. Toxicity data are essential for determination of the balance of risk and benefit and to determine the utility of therapeutic treatments.

We have found that crude extracts, such as infusions, prepared from Artemisia app, especially *A judaica,* have a positive mutagenic effect when tested in a conventional Ames type bacterial mutagenicity test. This mutagenicity is sufficient to preclude the development of the extracts as a commercial pharmaceutical product. When considering candidates for a potential pharmaceuticals, the therapeutic index (ratio of efficacy to toxicity) must be as high as possible. The present inventors have shown an extract to have activity in a chemically-induced rat model of Type 1 diabetes mellitus and in in vitro tests using isolated hepatocytes (liver cells). Surprisingly, they have been able to separate the efficacy and the mutagenicity to isolate a fraction from an Artemisia herb which has a significantly reduced mutagenic activity, whilst retaining the efficacy of the herb.

The present invention thus provides a purified extract of a plant from the Artemisia family which retains pharmaceutical efficacy while having lowered mutagenicity.

The invention also provides a pharmaceutical which is at least one composition of the invention, optionally in combination with a pharmacologically acceptable excipient. The pharmaceutical compositions of the invention may be suitable for oral or parenteral administration. The present invention further provides a method of a making pharmaceutical composition comprising mixing an extract, composition or compound of the invention with a pharmaceutically acceptable excipient.

The present invention also contemplates a method of treating hyperglycaemia, diabetes or other hyperglycaemic disorders of carbohydrate metabolism by administration of an extract or pharmaceutical composition of the invention. Also provided are methods of purifying an extract or compound according to the invention and the use of such extracts or compounds in the preparation of a medicament for the treatment of hyperglycaemia, diabetes or other hyperglycaemic defects of carbohydrate metabolism.

In the present invention a method is described of fractionating the extract to improve its utility by reducing its toxicity; while retaining its essential therapeutical benefit. By further fractionation it is possible to make extracts which have insulin-like activity and which have glucagon antagonist activity. Both of these activities are useful in a diabetes treatment for humans and animals. Using this method, it has been possible to produce extracts which have the required balance of insulin-stimulating and glucagon-antagonising actions to provide a treatment for DM. Surprisingly it has been found that both of these activities are desirable for optimum anti-diabetic activity in animals and humans.

Species related to *Artemisia judaica* are known to have been used in other ethnic cultures for similar purposes, but the toxicity attending such use is unacceptable. The data provided here show that gradient extraction of a plant extract yields fractions with anti-diabetic activity which retain the clinically useful action and have reduced toxicity.

Additional experimental work has provided further elucidation of fractions obtained from a concentrated aqueous extract of Artemisia spp. Surprisingly, it proved possible by using other chromatographic mobile phases; graded by altering the concentration of at least one component, to further fractionate. This reveals two or more fractions; one of which is flavonoid, glycoside- and polysaccharide-rich, and the other a terpenoid- and triterpenoid-rich fraction. Both have been tested for isulinomimetic and glucagon antagonist activity. The fraction which contains predominantly flavonoids (including glycosides) is insulinomimetic and is not eluted when the column is washed with water. This allows unabsorbed water-soluble material which is inactive in the GPa test to be removed. When the concentration of methanol in the eluting solvent (mobile phase) is increased, preferably in a stepwise fashion, most of the flavonoids are eluted at concentrations up to 40% methanol v/v; none were detected in the 70% fraction. Fractions eluted at methanol concentrations between 60% and 70% alcohol had optimal glucagon antagonist activity. By the use of a stepwise increase in alcohol concentration in the mobile phase, it is possible to effect a separation of fractions having respectively predominantly insulin-like and glucagon antagonist activities. It is thought that the 20–50% fraction contains triterpenoid components.

A method for preparing an anti-hyperglycaemic or anti-diabetic compound or extract according to the invention may comprise the steps of extraction of *Artemisia judaica, Arte-*

*misia herba-alba* or another herb of the Artemisia family with water, concentration to give a dry extract, washing with alcohol, preferably a lower aliphatic alcohol such as ethanol, chromatographic separation on e.g. a silica gel or an ion exhange column, elution with buffer and, optionally, processed further by concentration of the resulting solution or by drying. Desirably 100 g of Artemisia herb are extracted with water to give 12–20 g of dried extract.

The fractions eluted from the chromatography column may be analysed for anti-hyperglycaemic activity for example in an in vitro test such as those discussed herein and the active fractions combined for further processing, or processed separately. Alternatively, once the active fraction (s) have been identified, repetitive or batch processes may be employed to extract selectively or only those fractions from the plant. Drying may be by evaporation at elevated temperature and reduced pressure, e.g. at 30–45° C., preferably 35–40° C. or at 50° C.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors.

A composition may be administered alone or in combination with other treatments, either simultaneously or sequentially. For example, the present invention may provide a pharmaceutical composition for use as an adjunct to insulin therapy.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or parenteral e.g. by injection (cutaneous, subcutaneous or intravenous), or by administration to the buccal or nasal mucosae.

Formulations may be such as to provide a sustained release preparation for oral or parenteral use, such as by trans-dermal administration.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Insulin can have a direct effect on the liver, for example can influence steroid metabolism in isolated rat hepatocytes. By investigating the effect of the Artemisia extract on isolated hepatocytes, one can compare the biological effects of insulin and the extract. In the work leading to the present invention, the in vivo anti-diabetic activity of *Artemisia judaica* extracts has been tested in STZ diabetic and control rats, and these in vivo investigations complement hepatic Gpa activity tests in isolated hepatocytes.

Further details and aspects of the present invention will be apparent from the following examples and Figure which are presented by way of illustration and not limitation.

EXAMPLE 1

Figure 1:
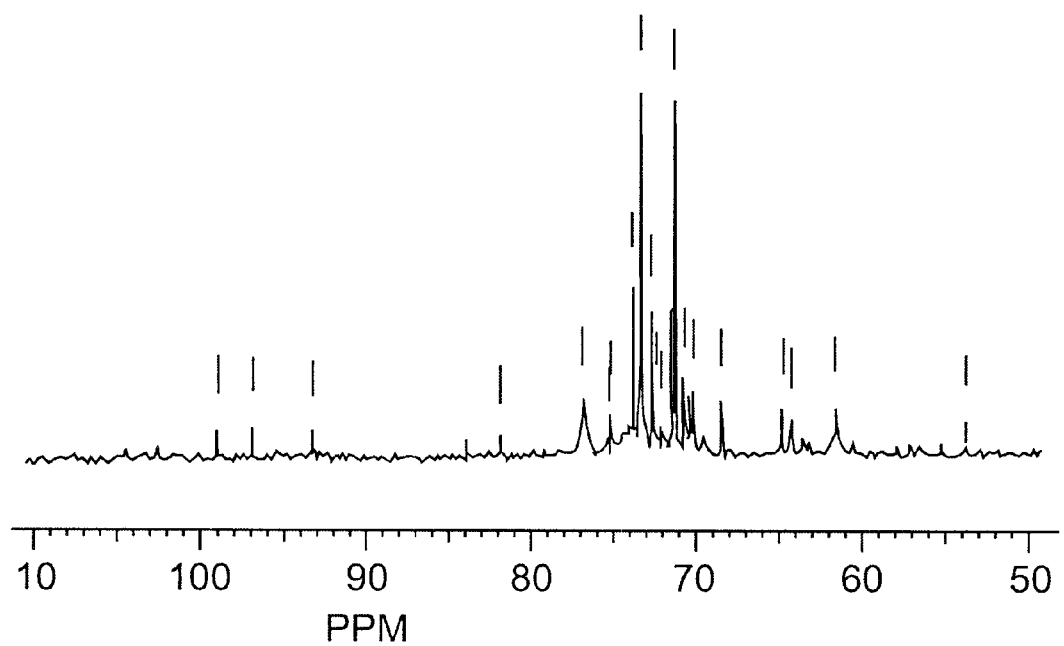
FIG. 1 shows a deuterium NMR trace showing carbon atoms in a sample of Extract 3 (Example 4).

*Artemisia judaica*, grown in Libya, was air dried and botanically identified. 100 g of whole dried plant was crushed in a pestle and mortar to a fine powder. The powder was mixed with 500 ml of distilled water, and allowed to macerate overnight at room temperature. The resultant dark green-brown mixture was filtered through filter paper (Whatman No. 1) and the clear filtrate evaporated to dryness at 40° C. under reduced pressure in a Buchi Rotavapor-R rotary evaporator. The resultant brown powder weighed 16 g. The residue was redissolved in distilled water at a concentration of 0.2 g/ml and frozen at −20° C. until required.

This extract, referred to as Extract 1 or Fraction 1, was tested in rats rendered diabetic by administration of Streptotozocin (STZ), and in in vitro tests for insulin-like activity. Toxicity was tested in a bacterial (Ames) mutagenicity test.

*Escherichia coli* and *Salmonella typhimurium* were used in the Ames test (B. N. Ames, J. McCann, E. Yamasaki— *Mutation Res.* 31 (1975) 347). The bacteria used carry a mutation which makes them dependent upon the presence of a specific nutrient medium for growth. If the test substance added to the growth medium of a plate of such bacteria is mutagenic, then a small proportion of the mutations it induces will cause the nutrient dependency mutation to revert, so that the bacteria will synthesise the nutrient and grow even in its absence. Observing whether colonies grow on nutrient deficient plates in the presence and absence of the test substance will thus reveal whether the substance is mutagenic and can give a measure of the mutagenicity of the substance.

Since many substances do not exert their mutagenic effect until they have been metabolised by enzyme systems not available in the bacterial cell, the test substance and the bacteria are incubated together with a liver fraction. Table 3 shows that Extract 1 was positive for mutagenicity in this liver supplemented Ames test.

TABLE 3

Antidiabetic activity of Extracts

| TEST, Animals | | Extract 1 | Extract 2 | Extract 3 Dose, Route | Insulin | Inositol |
|---|---|---|---|---|---|---|
| STZ Diabetic Rats | Controls | 200 µg/ml po | 10–120 µg/ml po | 1 ng/ml po | 1 ng/ml sc | 100–100 µg/ml |
| Excessive food intake | Normal * | reversed | reversed | reversed | reversed | ND |
| Weight gain | Normal * | normalised | normalised | normalised | normalised | ND |
| Diuresis | None * | reduced | reduced | reversed | reduced | ND |
| Glucosuria | Trace * | reduced | reduced | reversed | reduced | ND |
| Ketonuria | None * | reduced | reduced | reversed | reduced | ND |
| Activity of liver cells | | | | | | |
| Steroid metabolism | Normal *** | restored ** | restored | restored *** | restored * | negative |
| Glycogen Phosphorylase a activity | Normal *** | decreased *** | | decreased *** | decreased *** | negative |
| Effect on glucagon response | Normal *** | reversed ** | | reversed | reversed *** | ND |
| Rat toxicity limit dose | | >2 g/kg | | ND | ND | |
| Bacterial mutagenicity | | positive | positive | negative | negative | ND |

\* p ≦ 0.05 compared to STZ treated rats;
\*\* p ≦ 0.01 compared to STZ treated rats;
\*\*\* p = 0.001 compared to STZ treated rats
ND Not Determined Table 3 shows the symptoms produced in STZ-treated rats, similar to those of diabetes, and the difference in laboratory test values between control and STZ treated animals, which was statistically significant at a level of probability p≦0.05 or better. Extract 1 reversed the effects of STZ treatment at a dose level of 200 µg/ml given in the drinking water of these animals and these differences were statistically significant (p≦0.05 or better).

Urine was tested for the presence of ketones and glucose using Keto-Diabur Test 5000 sticks (Boehringer Mannheim, Lewes, UK). Glucose was assayed by the glucose oxidase method as described by Trinder (1969) using a kit supplied by the Sigma Chemical Co Ltd, Pool, UK)

The in vivo Tests

The effect of treatment with Artemisia on STZ-treated (diabetic) and control (non-diabetic) rats was studied. Artemisia appeared to act as a mild diuretic in the controls, increasing urine production from 9–14 ml to 12–25 ml in the 6 animals tested. The urine production for each animal was increased (p<0.05; paired t-test). Fluid intake, however, did not rise by a similar amount (26∓7 ml control v 21∓6 ml Artemisia). Bodyweight gain and food intake were unaffected by Artemisia treatment (weight gain: 15∓3 g control, 15∓1 g Artemisia; food intake: 25∓5 g/day control, 25∓kg/day Artemisia). There were no detectable ketones in the urine of any of the control animals treated. Urine glucose concentration was likewise unaffected by Artemisia treatment (0.37∓0.04 control; 0.31∓0.05 Artemisia).

The Effect of Artemisia on Diabetic Animals

The animals were monitored for 7 day periods before being made diabetic, after induction of diabetes by administration of STZ and during Artemisia treatment, so that each animal acted as its own control. Food intake rose after induction of diabetes and fell again following treatment with Artemisia. Urine volume showed a dramatic increase following induction of diabetes, an effect which was also reversed by treatment with Artemisia. Urine glucose levels rose dramatically after inducted of diabetes and fell significantly after Artemisia treatment. Ketone bodies were not detected in the control period but appeared after streptozotocin treatment and disappeared again following Artemisia treatment. Thus, the Artemisia treatment reversed all of the effects of induction of diabetes in the in vivo experiments.

At the 200 µg/ml concentration used above for in vivo tests, Extract 1 was submitted to in vitro tests of Gpa activity in isolated rat hepatocytes, the extract was active and had a similar degree of activity to that of insulin tested at a concentration of 1 ng/ml.

Isolated hepatocytes were prepared from control animals by a modification of the double perfusior technique of Seglen (1973) involving anaesthetising he animal with halothane/nitrous oxide and inserting a cannula into the hepatic portal vein. The liver was subsequently perfused first with a calcium-free buffer and then with collagenase solution. The isolated cells were freed from the connective tissue by gentle combing. Hepatocytes were suspended in Ham's F-10 nutrient solution, Williams' medium E or Krebs-Henseleit medium depending on the assay to be performed.

Assay for Glycogen Phosphorylase a Activity

Glycogen phosphorylase a activity, as an index of insulin-like or glucagon antagonist activity can be measured using falling logarithmic concentrations of analyte in the presence or absence of insulin or glucagon.

Isolated hepatocytes, suspended in Krebs-Henseleit solution at a concentration of $10^6$ cells/ml, were treated with Artemisia extract at a concentration of $2 \times 10^4$ g/ml (final concentration) in the presence or absence of insulin ($10^{-7}$M) or glucagon ($110^{-7}$M) for 2 minutes in a shaking water bath at 37° C. under constant oxygenation with 100% oxygen. The cells were subsequently centrifuged for 30s in a Beckman Microfuge and the pellet resuspended in MOPS buffer (pH 6.5) containing sodium fluoride (12.6 g/l), EDTA (1.85 g/l) and a dithiothreitol (0.31 g/l) at $10^6$ cells/ml. The suspended cells were homogenised in a Potter-Elvehjem homogeniser and the homogenate centrifuged at 300×g in a Damon-IEC refrigerated centrifuge at 4° C. for 10 minutes. The resultant supernatant was used to assay for glycogen phosphorylase a activity as described by Preiksatis & Kunos (1979). This technique involves the measurement of [$^{14}$C] glycose-1-phosphate to glycogen conversion in the presence of caffeine to inhibit glycogen phosphorylase b activity.

The effects of Extract 1 on steroid metabolism in liver cells was also studied.

Assay for Xenobiotic- and Steroid-Metabolising Enzyme Activities

The animals were killed by $CO_2$ asphyxiation and the liver quickly exised and placed in ice-cold buffer (0.1M phosphate buffer, pH 7.4). The liver was homogenised using a Potter-Elvehjem homogeniser with a teflon pestle and microsomes were prepared by differential centrifugation. The microsomes were resuspended by gentle homogenisation in the same buffer. The protein content was measured by the method of Lowry using bovine serum albumin as standard and the microsomes were diluted by 10 mg protein/ml.

The diluted microsomes were assayed for aniline 4-hydroxylase activity and aminopyrine N-demethylase activity (results not shown) and for androst-4-ene 3, 17-dione metabolism using published methodology.

The androst-4-ene 3, 17-dione metabolism in isolated hepatocytes was assayed using the method previously described by Hussin & Skett (1986).

As can be seen from Table 3, Extract 1 restored normal steroid metabolism to animals in which this had been disrupted by the onset of STZ-induced diabetes.

EXAMPLE 2

100 g of powered *Artemisia judaica* herb was macerated in purified water overnight (16 h), filtered and the clear solution evaporated to dryness. The dark green extract so produced was further extracted with 500 ml of 95% ethanol for 30 minutes in a Soxhlet apparatus, and the alcohol discarded. 9.8 g of a pale green powder (Extract 2) was produced and tested as described above for Extract 1.

Table 3 shows that Extract 2 retains the characteristic anti-diabetic activity of Extract 1 at a proportionately lower does when adjustment is made for the higher concentration of the extract. This extract was mutagenic in two strains of *E. coli* in the conventional Ames bacterial mutagenicity test.

EXAMPLE 3

20 g of Extract 2 was loaded onto a silica gel column 5 cm(diameter)×approx 28 cm (length) and eluted (under gravity) with a chloroform/methanol/water gradient (chloroform reducing from 100% (fraction 1) to 0% 95% (fractions 49–63), methanol rising from 0% (fraction 1) to 95% (fraction 49) and falling to zero again by fraction 61, water rising from 0% in fractions 1–29 to 100% in fractions 61–63). The 63 fractions of 100 ml were taken and the in vitro anti-hyperglycaemic activity of each was determined by the Gpa activity in isolated rat hepatocytes, as above. A peak of high activity was observed across fractions 34–44, with some activity at a much lower level also being observed in fractions 18, 19, 24, 52, 54 and 56. Fractions 1–14 showed a negative glucagon activity.

When tested (in vivo and in vitro) as in Examples 1 and 2, active fractions (Extract 3) showed qualitatively similar effects to those shown by insulin. Extract 3 represents an approximately 1,000-fold concentration of Extract 1 and this potency relationship is shown in its effectiveness in tests as shown by the results set out in Table 3.

Extract 3 approaches insulin in quantitative potency (1–10 ng/ml) in the tests used herein to indicate useful antidiabetic activity, and has the advantage of being active when administered orally. It is also active when given by injection (results not shown).

Surprisingly, when tested in the Ames test described above, at a dose of 1,000,000 ng (1 mg) per plate, Extract 3 was found to be non-mutagenic in bacteria. It therefore is potentially useful in the oral treatment of diabetes and other occurrences of hyperglycaemia in humans.

EXAMPLE 4

Fraction 35 from the chromatography elution was chosen as the basis for further characterization and was evaporated in a rotary evaporator at 35–40° C. and under reduced pressure to give 190 mg of a pale brown-coloured liquid (Extract 3). This was submitted to elemental and two-dimensional NMR analysis. Deuterium NMR was carried out at room temperature on a Bruker AM200SY machine.

The extract appeared to be chromatographically pure, contains only C, H and O and has a formula weight of about 180. The NMR (FIG. 1) indicates a structure typical of carbohydrate, probably a mainly sugar-based material and there are probably three anomeric hydroxyl groups (as indicated by the peaks at shifts of 93–102 ppm)

EXAMPLE 5

Inositol (also known as meso-inositol, myo-inositol and cyclohexitol) with the formula $C_6H_{12}O_6$ and a formula weight of 180.2, is a growth factor and vitamin of the B complex which his widely distributed in plants and animals.

Inositol obtained commercially was tested in the in vitro liver cell system described above at levels of up to 1 mg/ml. From Table 3 it can be seen that inositol was inactive even at this highest dose level.

It is therefore concluded that the active principle of *Artemisia judaica* is not meso-inositol and this is supported by a series of studies reported in The Lancet of May 20, 1989 (Vol. I pages 1113–4), in which it was shown that there was no evidence that dietary supplementation with meso-inositol improved nerve function in the management of complications of diabetes mellitus.

From the above experiments it is apparent that a crude extract and a partially purified extract of Artemisia have some insulin-like activity in isolated hepatocytes and in STZ-treated rats, but both of these extracts showed a positive mutagenic effect when tested in a conventional Ames-type bacteria mutagenicity test.

Surprisingly, it has been possible to purify an extract which we have defined by physico-chemical properties including formula weight, elemental analysis and two-dimensional NMR, which is much less mutagenic and yet retains the anti-diabetic activity of the herb. The potency of the extract (approximately 1,000-fold that of the crude herb in a mass for mass comparison) means that it has utility in the preparation of formulations for oral and parenteral use in the treatment of diabetes and other hyperglycaemic conditions in humans.

The following Examples illustrate the separation of distinct activities in various fractions.

EXAMPLE 6

One part of A judaica wad decocted with five parts of water at 90° C. and filtered; this extract is referred to as fraction F1. 0.5 ml of filtered decoction was process through a 500 mg bed volume of a reverse phase $C_{18}$ end capped grade of silicon dioxide from IST Ltd; $C_{18}$ (EC) is a suitable grade of material for this purpose although other materials with a similar specification can be used. Distilled water was passed through the loaded column until the eluent was colourless. The column was then eluted sequentially with 2 bed volumes of aqueous alcohol mixtures containing 20%, 30%, 40%, 50%, 60%, 70%, 80% and 100% ethanol. Each wash solution was allowed to run into the sorbent bed before the next solution was applied. The final concentration of alcohol in the mobile phase at each step gradient is approximate and in this example a mean value is given.

Each fraction was carefully evaporated to dryness and weighed in a tared vessel. The dried samples were redissolved in methanol (100 µl) and (100 µl of $H_2O$ for the void volume) and subjected to chromatography. Aliquots were also removed for glycogen phosphrylase a activity determinations.

Figure 2A:
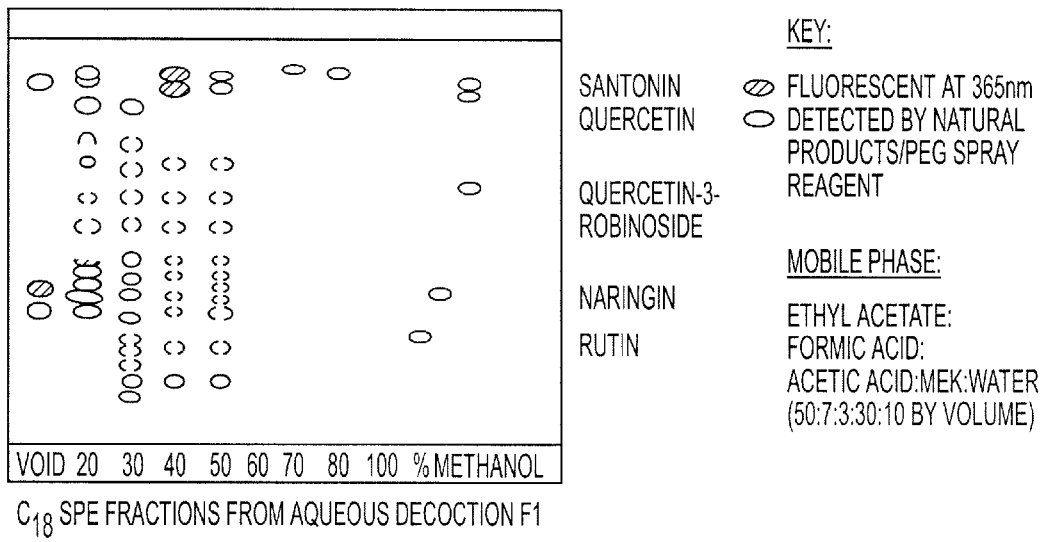
FIGS. 2a, 2b and 2c are traces of various fractions (see Example 6).

FIGS. 2(a–c) shows the results obtained by thin layer chromatography (TLC) of extract F1 eluted with progressively higher concentrations of methanol. Chromatograms were developed in solutions which are known to give good resolution of particular classes of plant constituents as follows:

FIG. 2a Eluting solvent—Ethyl acetate:formic acid:methyl ethyl ketone:water (50:7:3:30:10 by volume).

Colour development:Natural products/polyethylene glycol (NP/PEG) spray.

Visualisation: UV 365 nm, fluorescent spots are shown with hatching; open circles indicate colours (usually yellow to orange coloured spots).

This TLC shows the presence of flavonoids in the 30–50% fractions of F1.

Figure 2B:
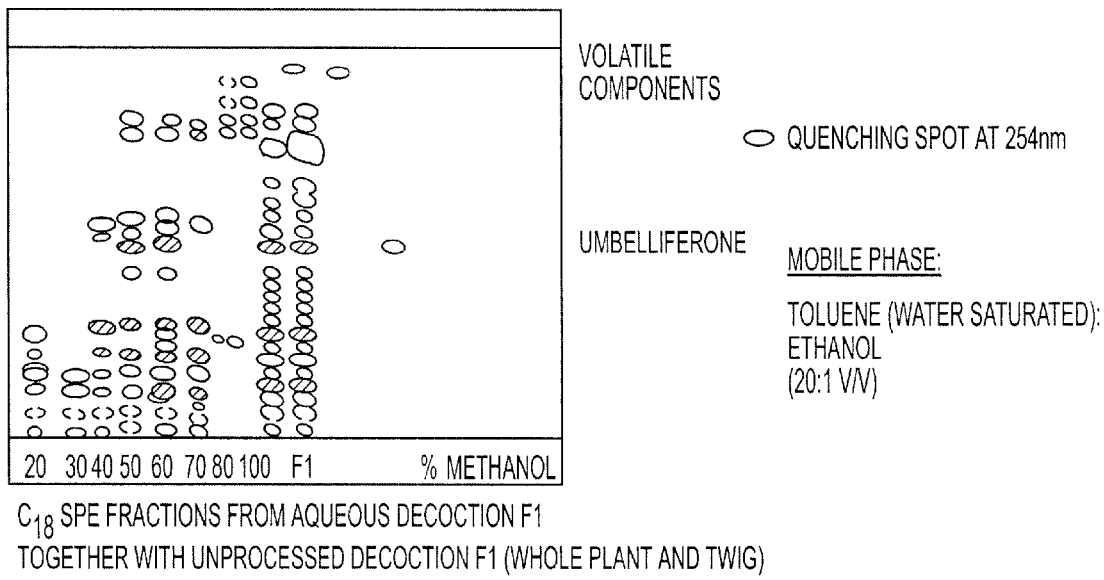

FIG. 2b Eluting Solvent—Toluene (water saturated):ethyl alcohol (20:1 v/v).

Visualisation: UV 254 nm (quenching with solid spots) and 365 nm for fluorescent spots (hatched).

This TLC shows the presence of a group of components with $R_1$ values greater than 0.78 in the 50%–80% fractions. These components exhibit TLC behaviour typical of volatile terpenoids. The fluorescent compound with an $R_f$ value of approximately 0.54 co-chromatographs with umbelliferone—confirmed by high pressure liquid chromatography (HPLC) evidence.

Figure 2C:
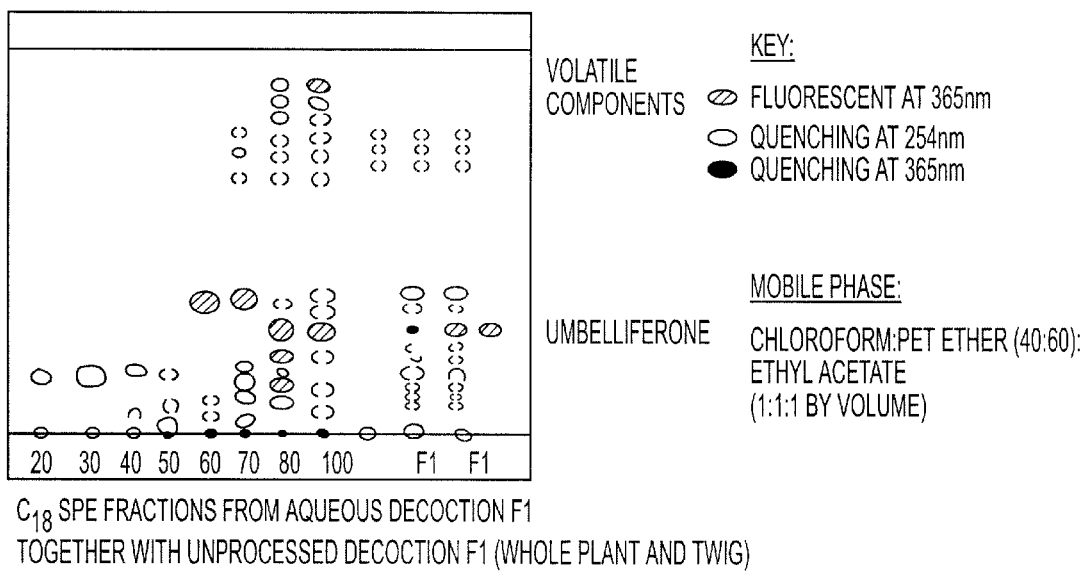

FIG. 2c Eluting solvent—Chloroform:petroleum ether 40/60:ethyl acetate (1:1:1 v/v).

Visualisation: UV 254 and 365 nm. In this eluting solvent compounds with $R_f$ values of approximately 0.09–0.22 are characteristic of glucoiridoids (sesquiterpene lactones), and these were most abundant in fractions 70% and 80%.

EXAMPLE 7

Solutions produced in Example 6 by stepwise gradient elution of fraction F1 were analysed by HPLC.

Gradient Elution: from acetonitrile:water (10:90 to 90:10)

Column: Spherisorb EOD-S2 (15×046 cm)

Flow Rate: 1.0 ml/minute

Detection: UV at 262 nm, 0.1 AUFS

Injection Volume: Equivalent to 5 µl of F1

HPLC traces show peaks with retention times of up to 25 minutes which are characteristic of water soluble/polar compounds such as flavonoids, coumarins and their glycosides. These were most abundant in the 30–50% extracts of F1.

Sugar conjugates of (for example) umbelliferone, with an $R_T$ of 22.5–23 minutes were detected in F1 fractions eluted with 50 and 60% methanol.

Sesquiterpene lactones, eluting in the 28–36 minute range (cf Santonin, $R_T$ 36.5 min) were absent in fractions 30–50% and present in the 60–80% fractions of F1.

Flavone components and terpinoid volatile constituents elute with an $R_F$ of more than 37 mins. Piperitone ($R_T$ 45.5–46.5 mins) was detected in the 60–80 methanol extracts of F1; namely, a flavonoid/glycoside-rich fraction extractable at alcohol concentrations up to 50% and particularly up to 30%, having insulinomimetic activity.

Sequential extraction of these fractions, which entails removal of unwanted materials, provides a process for making an effective and less toxic preparation for treatment of Diabetes mellitus.

In Table 4, the TLC and HPLC chromatographic behaviour of stepwise gradient extracts of F1 are summarised together with relevant biological activity. Fractions with insulinomimetic activity are those produced by extraction of F1 with concentrations of up to 50% methanol v/v. This fraction contains predominantly flavonoids and their glycosides, coumarins and some triterpenoids. To ensure maximal separation of these fractions a cut-off at 30% and 70% alcoholic concentration has been employed.

Fractions with glucagon antagonist activity were those produced by extraction of F1 with 70–80% methanol. It has been shown by direct experiment that the volatile fraction which can be obtained from Artemisia by distillation also has glucagon antagonist activity and constituents in this fraction may be those present in the oil.

Table 4 shows the insulinomimetic activity and glucagon antagonist activity of the fractions extracted at various alcoholic concentrations using a 2 ml aliquot of an aqueous extract prom aerial parts of A. judaica.

TABLE 4

| | | | TLC Characteristics | | | HPLC | | Biological Activity | |
|---|---|---|---|---|---|---|---|---|---|
| Fraction (% Methanol) used to Extract | Wt of Dry Extract (%) (a)[1] | Appearance | Flavonoids & Coamarite | Triterpenoids | Unidentified Quenching at 254 nm | Flavones & Volatiles | Polar Glycosides & Flavonoids | Insulinomimetic | Glucagon Antagonist |
| 0 | 4.5 | Yellow solid | ± | – | – | – | – | – | – |
| 20 | 2.0 | Yellow solid | ++ | + | – | – | – | – | – |
| 30 | 1.8 | Yellow solid | +++ | ++ | – | – | + | +++ | – – |
| 40 | 1.6 | Yellow solid | +++ | +++ | – | – | + | ++ | ± |
| 50 | 1.6 | Light | ++ | ++ | – | – | + | ± | + |
| 60 | 1.1 | Yellow oil | + | ± | ++ | + | – | – | ++ |
| 70 | 0.9 | Light yellow oil | – | – | ++ | + | – | – | +++ |
| 80 | 0.5 | Light yellow oil | – | – | + | – | – | + | ± |
| 100 | 0.7 | Colourless Oil | – | – | – | – | – | – | – |

TLC = Thin Laye Chromatography
HPLC = High Pressure Liquid Chromatography
– = No activity compared to negative control
± = Trace of activity compared to negative control
+ to +++ = Significant, dose-dependent activity
Weights are expressed as a percentage of the weight of F1

Solid phase extraction (SPE) is analogous to liquid/liquid extraction. As a solution of various components migrates through an SPE column, compounds are extracted (or retained) by the sorbent material in the column. Interfering substances can be selectively removed from the column by the judicious choice of wash solvents. Desirable compounds or groups of compounds may be selectively eluted (or recovered) from the column by an elution solvent, resulting in highly purified extracts. Manipulation of elution volume can result in significant concentration being achieved. The technique is capable of a high degree of automation and may be scaled up to produce the quantities required for commercial use of the invention. Alternatively, a batch process can be used as described in Example 8.

In whole animals, made diabetic with ST2, anti-diabetic activity with the "30%" or "70%" fraction (Fractions 2A & 2B) was not markedly high when each extract was given alone. Surprisingly, optimum anti-diabetic activity is produced in diabetic animals when the fractions showing ex vivo insulinomimetic and glucagon antagonist activity in hepatocytes are given together.

EXAMPLE 8

A process for manufacture of an extract which can be used in pharmaceutical compositions for the treatment of diabetes is based on the admixture of fractions having both insulinomimetic and glucagon antagonist activity.

On the laboratory scale, methanol/water was used as eluent; similar results were obtained using ethanol/water mixtures. In pharmaceutical manufacture where the solvent is to be completely removed from the product, it will be obvious to those skilled in the art that industrial Methylated Spirit, which is a mixture of ethanol and methanol, can be used for fractionation of the extract. References to "spirit" in this Example indicate the use of methanol, ethanol or a mixture of the two in the form of Industrial Methylated Spirit. Isopropanol can alternatively be used.

10 kg of *Artemisia judaica* in coarse powder were heated with 2 liters of water in a vessel fitted with a water-cooled condenser, and 1 liter of distillate was is collected and reserved.

50 liters of boiling water were added to the residual vegetable, and allowed to macerate for one hour, after which the liquid was removed by straining (filtration or centrifugation could be used). The solution was concentrated to a volume of 4 liters and added, with the reserved distillate, to 25 kgs of $C_{18}$ reverse phase modified silicon dioxide and stirred for 30 minutes. The supernatant solution was separated by filtration or centrifugation and the silicon dioxide was washed twice with 10 liters of water. Industrial Methylated Spirit was added to bring the concentration to 30% (v/v). The suspension was stirred for 30 minutes and the supernatant solution separated by filtration. Two further 12.5 liter volumes of 30% v/v spirit water were used to wash the silicon dioxide suspension. The combined solutions were reserved and evaporated at low temperature with recovery of solvent to give Fraction 2A.

To the silicon dioxide cake, twice its bed volume of spirit was added, stirred for 15 minutes and centrifuged or filtered to remove the solution. The cake was washed with one bed volume of 70% spirit/water solution, twice, and centrifuged or filtered. The combined solution was evaporated at low temperature with recovery of solvent to give Fraction 2B.

Pharmaceutical compositions (including solid dosage forms such as tablets, hard and soft gelatin capsules, emulsions and solutions) can be made by combining Fractions 2A and 2B in the proportions 0.2:10 to 10:0.2, preferably in the ratio 0.5:2 to 2:0.5, with pharmaceutically acceptable exipients. This includes excipients for tableting, encapsulation for solid dosage forms, and by solution or emulsification to provide liquid dosage forms, using standard pharmaceutical formulation procedures.

The combined Fractions 2A and 2B, separately and together are less mutagenic than Extract 1 of Example 1.

It will be apparent to those skilled in the art that other separating techniques, using appropriate mixtures of solvent can be used to effect the separation of fractions 2A and 2B. Consideration of the appropriate tables of Langmuir Blodget's Isotherms ($E_0$) will reveal suitable solvents for this purpose.

The examples given above are based on the use of *Artemisia judaica* as the preferred Artemisia species. Some closely related species referred to in Table 2 contain qualitatively similar components, but differ in quantitative composition. A person skilled in the art will appreciate that the method described can be applied, with adjustment of quantities to the preparation of an anti-diabetic product from other desert-growing Artemisia spp.

The skilled man will be able, on the basis of the above disclosure and his common general knowledge, to develop methods for large-scale extraction to produce the compounds, compositions and extracts of the invention on a manufacturing scale.

All publications referred to herein are incorporated herein by reference in their entirety.

What is claimed is:

1. A process for preparing fractions of *Artemisia judaica* which are effective against diabetes in mammals and which have non-mutagenic properties when tested by the Ames method, the process comprising:

(A) preparing an aqueous extract of *Artemisia judaica*;
   (B) subjecting the extract to reverse phase chromatographic separation by eluting with an increasing percentage of alcohol to water gradient; and
   (C) collecting the eluent between 30 to 70% alcohol to water.

2. The process according to claim 1 wherein before the preparation of the extract volatile oils are distilled from the plant.

3. The process according to claim 1, wherein the chromatographic separation is carried out using a column or plate.

4. The process according to claim 3, wherein the chromatographic separation (B) is carried out on an alcoholic extract prepared by:

a) concentrating the aqueous extract to dryness; and
   b) treating the dry residue with alcohol.

5. A process for preparing fractions of *Artemisia judaica* which are effective against diabetes in mammals and which have non-mutagenic properties when tested by the Ames method, the process comprising:

(A) preparing an aqueous extract of *Artemisia judaica*;
   (B) subjecting the extract to reverse phase chromatographic separation by eluting with an increasing percentage of alcohol to water gradient;
   (C) collecting the eluent between 30 to 70% alcohol to water;
   (D) testing eluent fractions for (i) mutagenicity and (ii) insulinomimetic and/or glucagon antagonistic properties; and
   (E) selecting eluent fractions which respond negatively in the mutagenicity test and positively either for insulinomimetic behaviour or for glucagon antagonism as the fractions effective against defective carbohydrate metabolism.

6. The process according to claim 5 wherein before the preparation of the extract volatile oils are distilled from the plant.

7. The process according to claim 5, wherein the chromatographic separation is carried out using a column or plate.

8. The process according to claim 7, wherein the chromatographic separation (B) is carried out on an alcoholic extract prepared by:

a) concentrating the aqueous extract to dryness; and
   b) treating the dry residue with alcohol.

9. A process for screening fractions of *Artemisia judaica* which are effective against diabetes in mammals and which have non-mutagenic properties when tested by the Ames method, the process comprising:

(A) preparing an aqaueous extract of *Artemisia judaica*;
   (B) drying the extract;
   (C) washing the dried extract with 95% ethanol;
   (D) applying the extract to a silica gel chromatography matrix;
   (E) eluting with a chloroform, methanol and water gradient of increasing polarity, where chlorform is varied from 100% to 0%, methanol is varied from 0% to 95% to 0% and water is varied from 0% to 100%; and
   (F) collecting the fractions and testing for mutagenicity and anti-hyperglycemic activity.

* * * * *